United States Patent [19]

Mahn et al.

[11] Patent Number: 4,725,613
[45] Date of Patent: Feb. 16, 1988

[54] SYNERGISTIC MICROBIOCIDAL COMPOSITION CONTAINING A MIXTURE OF A N-ALKYLDIMETHYLBENZYL AMMONIUM HALIDE AND A BICYCLICPOLYOXYMETHYLENE OXAZOLIDINE

[75] Inventors: Frederick R. Mahn, Verona; Lora J. Bogdany, Denville; Joseph J. Baron, Morris Plains; Edward G. Knapick; Edward M. Antonucci, both of Randolph, all of N.J.

[73] Assignee: Drew Chemical Corporation, Boonton, N.J.

[21] Appl. No.: 63,154

[22] Filed: Jun. 17, 1987

Related U.S. Application Data

[63] Continuation-in-part of Ser. No. 894,265, Aug. 6, 1986, abandoned.

[51] Int. Cl.[4] .................. A01N 33/12; A01N 43/76
[52] U.S. Cl. .................................... 514/375; 514/643
[58] Field of Search .................................. 514/643, 375

[56] References Cited

U.S. PATENT DOCUMENTS 4,135,945  1/1979  Buono et al. ..................... 106/300
4,173,643 11/1979  Law ................................... 514/372

Primary Examiner—Allen J. Robinson
Attorney, Agent, or Firm—Walter H. Schneider

[57] ABSTRACT

A synergistic microbiocide comprising a member selected from the group consisting of (1) an N-alkyl ($C_8$–$C_{30}$) dimethylbenzylammonium halide and (2) a polycondensation product of acrolein/formaldehyde in a molar ratio of 1:10–10:1 in combination with (3) a bicyclic polyoxymethylene-oxaazolidine having the formula:

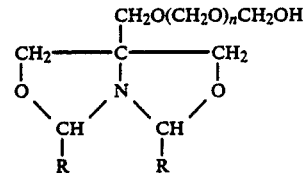

in which each R represents hydrogen, an alkyl of 1–6 carbons, phenyl, halophenyl or —$(CH_2O)_mCH_2OH$ in which m is 0–2 and n is 0–4, the ratio of (1) or (2) to (3) being 1:10–10:1 by weight.

2 Claims, No Drawings

SYNERGISTIC MICROBIOCIDAL COMPOSITION CONTAINING A MIXTURE OF A N-ALKYLDIMETHYLBENZYL AMMONIUM HALIDE AND A BICYCLICPOLYOXYMETHYLENE OXAZOLIDINE

This application is a continuation-in-part of application Ser. No. 894,265 filed Aug. 6, 1986 now abandoned.

BACKGROUND OF THE INVENTION

1. Field of the Invention

The present invention relates to inhibiting the growth of bacteria in various industrial environments. More particularly, the present invention relates to an improved microbiocidal composition and its method of use. Still more particularly, the present invention relates to a synergistic microbiocidal composition, and its method of use, the composition comprising a combination of (1) an N-alkyldimethylbenzyl ammonium halide, or (2) a polycondensation product of acrolein and formaldehyde, and (3) a bicyclic polyoxymethyleneoxazolidine.

2. Description of the Prior Art

The presence of organic materials in the manufacture and/or use of various aqueous systems such as latices, adhesives, paints, coatings, mineral slurries and the like renders them susceptible to deterioration by virtue of exposure to bacteria and other microorganisms existing in the particular environment. It is, therefore, a conventional practice to seek to inhibit the microbial deterioration of such systems by incorporating therein any of various materials or combinations of materials that are characterized by having antibacterial activity.

Numerous materials have been found to possess such antibacterial activity. For instance, various quaternary ammonium salts having this activity are disclosed in U.S. Pat. No. 4,479,820; various acrolein/formaldehyde polycondensation products are disclosed in U.S. Pat. No. 4,501,668; and various polyoxymethyleneoxazolidines are disclosed in U.S. Pat. No. 4,135,945. In addition, U.S. Pat. Nos. 3,231,509 and 4,173,643 disclose microbiocidal synergistic combinations comprising quaternary ammonium salts with respectively, bis(halomethyl)sulfones and 4-isothiazoline-3-ones.

SUMMARY OF THE INVENTION

It is a principal object of this invention to provide an improved microbiocidal composition. It is a further object of this invention to provide an improved microbiocidal composition that is storage stable, and which is compatible with a variety of systems susceptible to biocidal degeneration thereby permitting its use without objectionable and/or unacceptable by-product odor, discoloration, thickening and the like. A further object of this invention is to provide an improved microbiocidal composition that is cost effective, i.e., performs effectively on the basis of its cost per unit weight and duration of its effectiveness on the treated system. Another object of this invention is to provide an improved method of inhibiting bacterial growth in a variety of systems in industry and commerce.

DESCRIPTION OF THE PREFERRED EMBODIMENT

These objects have been met in accordance with this invention by a composition comprising (1) an N-alkyldimethylbenzylammonium halide in which the alkyl has a carbon chain length of $C_8$ to $C_{30}$, or (2) an acrolein/formaldehyde condensation product having a molar ratio between 1:1 and 1:10, in combination with (3) a bicyclic polyoxymethyleneoxazolidine having the formula:

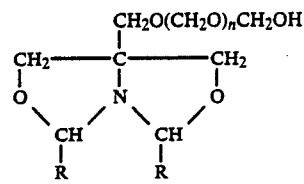

in which each R represents hydrogen, an alkyl of 1-6 carbons, phenyl, halophenyl or —$(CH_2O)_m CH_2OH$ in which m is 0-2 and n is 0-4.

Preferably, the quaternary ammonium salt (Component 1) is an N-long chain alkyl ($C_{12}$: 40%; $C_{14}$: 50%; $C_{16}$: 10%) dimethylbenzyl ammonium chloride obtained commercially under the trademark Hyamine ®3500 from Lonza, Inc.

The acrolein/formaldehyde condensation product (Component 2) is produced by the condensation of acrolein and formaldehyde in a preferred molar ratio of 1:2 to 1:4 in an aqueous or aqueous/organic medium in the presence of a basic catalyst. Such a polycondensation product is available commercially under the trademark Formac ®40 from Degussa.

The preferred bicyclic polyoxymethyleneoxazolidine (Component 3) is a mixture comprising:
(a) 35% 5-hydroxymethyl-1-aza-3,7-dioxabicyclo(3.3.0)-octane,
(b) 48% 5-hydroxymethoxymethyl-1-aza-3,7-dioxabicyclo-(3.3.0)-octane, and
(c) 16% 5-hydroxymethyl poly[oxymethylene($C_2$: 74%; $C_3$: 21%; $C_4$: 4%; $C_5$: 1)]-1-aza-3,7-dioxabicyclo-(3.3.0)-octane.

The preferred bicyclic polyoxymethyleneoxazolidine is available commercially under the trademark Nuosept 95 from Nuodex ®, Inc.

In the practice of the invention, the quaternary ammonium salt or the polycondensation product is used in combination with the bicyclic polyoxymethyleneoxazolidine in a range of 1:10-10:1 by weight, preferably in a ratio range of 1:3-3:1. The composition can be employed in the form of a dilute aqueous or non-aqueous solution and can be added to the aqueous system to be treated in any conventional way in an amount effective to inhibit microorganic growth. Generally, the effective concentration will range from as little as 100 ppm to as much as 5000 ppm depending upon the nature of the system being treated. In general, a concentration on the order of 500-2000 ppm will be found adequate.

In order to demonstrate the synergistic microbiocidal activity of the compositions of this invention, the following Example was conducted. All parts are by weight unless otherwise noted.

EXAMPLE

An unpreserved sample of styrene-butadiene-vinylidene chloride (SBVC) latex was analyzed for microbial content before being utilized for preservation evaluation according to this invention. It was determined that the latex sample was free of contamination.

The uncontaminated, unprotected SBVC latex was divided into 50 gr. aliquots and dosed with the microbiocide compositions of this invention as reported in the following Table. Each of the components of each of the compositions was also separately tested as microbiocides while two aliquots remained untreated to serve as controls.

The challenged inoculum was a pooled suspension of microorganisms comprising the bacteria species Pseudomonas, Bacillus and Penicillium that had been grown from contaminated latex material. All of the samples were challenged on a weekly basis for 4 weeks with 0.01 ml. of the pooled suspension containing at least $10^6$ organisms per ml. Following 72 hours of room temperature incubation, a 1 ml. quantity of each sample was transferred to 2 ml. of tryptic soy broth (TSB). The TSB tubes were incubated at room temperature for 24 hours and streaked onto TGE plates for growth of bacteria. After 48 hours incubation at room temperature, the plates were read and graded according to the description following the Table.

The tested compositions comprised combinations of Component 1/Component 3 and combinations of Component 2/Component 3. Component 1 was obtained commercially under the trademark Hyamine®3500 as an aqueous solution containing 80% active ingredient. Component 2 was obtained commercially under the trademark Formac®40 as an aqueous solution containing 40% active ingredient. Component 3 was obtained commercially under the trademark Nuosept®95 as an aqueous solution containing 50% active ingredient. The compositions according to this invention as well as the separately tested components were adjusted to an active ingredient content of 20%. Results appear in the following Table.

TABLE

| Biocide | Ratio | PPM | Weekly Growth Rate* | | | |
|---|---|---|---|---|---|---|
| | | | 1 | 2 | 3 | 4 |
| Components 1 and 3 | 1:3 | 500 | — | — | +2 | +2 |
| | | 1000 | — | — | — | — |
| | | 2000 | — | — | — | — |
| | 1:1 | 500 | — | — | — | +2 |
| | | 1000 | — | — | — | +1 |
| | | 2000 | — | — | — | — |
| | 3:1 | 500 | +1 | +2 | +4 | +4 |
| | | 1000 | — | — | — | +3 |
| | | 2000 | — | — | — | — |
| Components 2 and 3 | 1:3 | 500 | — | +1 | +1 | +1 |
| | | 1000 | — | — | — | — |
| | | 2000 | — | — | — | — |
| | 1:1 | 500 | — | +1 | +1 | +1 |
| | | 1000 | — | +1 | +1 | +1 |
| | | 2000 | — | — | — | — |
| | 3:1 | 500 | — | — | — | — |
| | | 1000 | — | — | — | — |
| | | 2000 | — | — | — | — |
| Component 1 | | 500 | +4 | +4 | +4 | +4 |
| | | 1000 | +4 | +4 | +4 | +4 |
| | | 2000 | +4 | +4 | +4 | +4 |
| Component 2 | | 500 | +1 | +1 | +1 | +2 |
| | | 1000 | — | +1 | +1 | +1 |
| | | 2000 | — | +1 | +1 | +1 |
| Component 3 | | 500 | +1 | +1 | +1 | +2 |
| | | 1000 | — | +1 | +1 | +2 |
| | | 2000 | — | +1 | +1 | +1 |
| Control #1 | | | +2 | +4 | +4 | +4 |
| Control #2 | | | +4 | +4 | +4 | +4 |

*The rating system for microbial growth on streaked, prepoured agar plates is as follows:

| Growth rate | Description |
|---|---|
| — | No growth; zero colonies |
| +1 | Maximum of 15 total colonies with no more than 5 of these having diameters of ⅛ inch |
| +2 | Sporadic growth on ½ total streaked area, remaining ½ area relatively clear; maximum of 20 total colonies with no more than 6 of these having diameters greater than ⅛ inch |
| +3 | Dense growth on ⅜-¾ of streaked area; minor colonies too numerous to count; 20 or more major colonies having diameters of ⅛ inch or larger |
| +4 | Uniform, dense growth over entire streaked area; colonies pinhead size or larger |

Reference in the disclosure to details of specific embodiments is not intended to restrict the scope of the appended claims, which themselves recite those features regarded as essential to the invention.

We claim:

1. A microbiocidal composition comprising a synergistic mixture the first component of which is N-alkyl ($C_{12}$: 40%; $C_{14}$: 50%; $C_{16}$: 10%) dimethylbenzyl ammonium chloride and the second component of which is a bicyclic polyoxymethyleneoxazolidine comprising a mixture of (a) 35% 5-hydroxymethyl-1-aza-3,7-dioxabicyclo-(3.3.0)-octane, (b) 49% 5-hydroxymethoxymethyl-1-aza-3,7-dioxabicyclo(3.3.0)-octane, and (c) 16% 5-hydroxymethylpoly[oxymethylene($C_2$: 74%; $C_3$: 21%; $C_4$: 4%; $C_5$: 1%)]-1-aza-3,7-dioxabicyclo(3.3.0)-octane, said first and second components being in a ratio of 1:3-3:1 by weight.

2. A method for inhibiting the growth of bacteria in an aqueous system which comprises adding to said system an amount of a microbiocidal composition according to claim 1 effective to inhibit the growth of bacteria.

* * * * *